US009591880B2

(12) United States Patent
Lee et al.

(10) Patent No.: US 9,591,880 B2
(45) Date of Patent: Mar. 14, 2017

(54) POST-SURGICAL GARMENT

(71) Applicant: Life in the Pink, Inc., Atlanta, GA (US)

(72) Inventors: Tonya E. Lee, Atlanta, GA (US); Ismary Susset Bryan, Suwanee, GA (US)

(73) Assignee: Life in the Pink, Inc., Atlanta, GA (US)

( * ) Notice: Subject to any disclaimer, the term of this patent is extended or adjusted under 35 U.S.C. 154(b) by 506 days.

(21) Appl. No.: 14/157,008

(22) Filed: Jan. 16, 2014

(65) Prior Publication Data

US 2014/0196189 A1    Jul. 17, 2014

Related U.S. Application Data

(60) Provisional application No. 61/753,330, filed on Jan. 16, 2013.

(51) Int. Cl.
*A61F 5/449* (2006.01)
*A41D 13/12* (2006.01)
*A61F 5/44* (2006.01)

(52) U.S. Cl.
CPC ........ *A41D 13/1245* (2013.01); *A61F 5/4408* (2013.01); *A61F 5/449* (2013.01)

(58) Field of Classification Search
CPC ............ A41D 13/1236; A41D 13/1245; A41D 13/1281; A61F 5/4408; A61F 5/449; A61F 2103/15073; A61F 2103/15154; A61F 201/15073; A61F 201/151543; A61M 25/02; A61M 2025/0206; A61D 2600/106

(Continued)

(56) References Cited

U.S. PATENT DOCUMENTS 4,533,355 A * 8/1985 Fair .................. A61F 5/445 2/238
4,666,432 A * 5/1987 McNeish ............. A61M 25/02 128/DIG. 26

(Continued)

FOREIGN PATENT DOCUMENTS

WO    WO03-024258    3/2003
WO    2014113579 A1    7/2014

OTHER PUBLICATIONS

Horton, Karen M., "Post-Operative Instructions," retrieved on Jan. 10, 2014 from www.drkarenhorton.com/patient-information/post-operative-instructions, pp. 1-15.

(Continued)

*Primary Examiner* — Lynne Anderson
(74) *Attorney, Agent, or Firm* — Johnson, Marcou & Isaacs, LLC

(57) ABSTRACT

A post-surgical garment comprises a wrap-around material with pouches for comfortable placement of surgical drains. The garment provides a wrap around piece designed to keep the post-surgical drains and the tubing of the drains secure while showering, sponge bathing or during daily activities. A post-surgical drain is slipped through an opening on the side of the garment and any attached tubing is fed through. The post-surgical drain and excess tubing is placed in a pouch. Flaps are securely closed to cover the opening. The garment is then closed in the front with a secure closure.

18 Claims, 3 Drawing Sheets

(58) Field of Classification Search
USPC .................................. 604/345, 353, 355
See application file for complete search history.

(56) References Cited

U.S. PATENT DOCUMENTS

| | | | |
|---|---|---|---|
| 4,873,982 A * | 10/1989 | Morrison | A41D 13/1245 600/300 |
| 5,403,285 A * | 4/1995 | Roberts | A61M 25/02 604/179 |
| 5,823,984 A | 10/1998 | Silverberg | |
| 6,048,252 A | 4/2000 | Sebring | |
| 6,055,668 A | 5/2000 | Gros et al. | |
| 6,206,854 B1 | 3/2001 | Weaver | |
| 6,390,885 B1 | 5/2002 | Brooks | |
| 6,477,710 B1 * | 11/2002 | Ojoyeyi | A41D 13/1236 2/114 |
| 6,681,404 B1 | 1/2004 | Adlard et al. | |
| 7,010,812 B1 * | 3/2006 | Cho | A41D 13/1245 2/104 |
| 7,396,272 B1 | 7/2008 | Newlen et al. | |
| 7,942,856 B2 * | 5/2011 | Lentini | A41D 13/1245 2/100 |
| 8,105,256 B1 | 1/2012 | Ariza | |
| 8,506,509 B1 | 8/2013 | Ariza | |
| 8,516,613 B2 * | 8/2013 | Crites | A41B 1/00 2/69 |
| 8,845,608 B2 * | 9/2014 | Krasikoff | A61M 27/00 604/345 |
| 2004/0167456 A1 | 8/2004 | Kingsford et al. | |
| 2004/0226073 A1 | 11/2004 | McCullar et al. | |
| 2005/0102731 A1 | 5/2005 | Beuk | |
| 2006/0064067 A1 | 3/2006 | Plauche et al. | |
| 2006/0173427 A1 | 8/2006 | Urbina et al. | |
| 2007/0113316 A1 | 5/2007 | King | |
| 2007/0271672 A1 | 11/2007 | Lentini et al. | |
| 2008/0294128 A1 | 11/2008 | Richards | |
| 2008/0312615 A1 | 12/2008 | Hunter et al. | |
| 2009/0024069 A1 | 1/2009 | Appel | |
| 2009/0100569 A1 | 4/2009 | Butler | |
| 2011/0196458 A1 | 8/2011 | Bratcher | |
| 2011/0219511 A1 | 9/2011 | Fishbein et al. | |
| 2012/0260393 A1 | 10/2012 | Crites et al. | |
| 2015/0320623 A1 | 11/2015 | Lee et al. | |

OTHER PUBLICATIONS

Baharlou, "International Preliminary Report on Patentability issued in International Application No. PCT/US2014/011874)", mailed Jul. 30, 2015, 10 pages.

Heo, "International Search Report and Written Opinion issued in International Application No. PCT/ US2014/011874)", mailed May 20, 2014, 13 pages.

Petrik, "Office Action issued in U.S. Appl. No. 14/273,296, filed May 8, 2014", mailed Mar. 24, 2016, 15 pages.

* cited by examiner

POST-SURGICAL GARMENT

RELATED APPLICATION

This patent application claims priority under 35 U.S.C. §119 to U.S. Patent Application No. 61/753,330, filed Jan. 16, 2013 and entitled "Wrap-Around Post Surgical Garment." The entire disclosure of the above-identified application is hereby fully incorporated herein by reference.

TECHNICAL FIELD

The present invention relates generally to post-surgical garments and more specifically to a wrap around water-resistant garment for men, women, and children who have had breast and/or torso surgery as a drain management garment.

BACKGROUND

After surgeries, such as mastectomies, breast augmentation, and or surgeries in the torso area, patients often are sent home with implanted drains and instructions not to get the surgical area wet. Therefore, many patients are left with the uncomfortable option of sponge bathing or showering with difficulty as to not get their bandages wet and nowhere to comfortably place their surgical drains. For some patients this condition can last up to four to six weeks.

Conventional mastectomy and compression garments are not designed for bathing, nor do they include pouches for drains. Per the drain manufacturer's suggestion, patients are instructed to pin drains to their clothing. However, during a shower, for example, there is nowhere to pin the drains.

To overcome the many limitations of the prior art, an improved post-surgical garment is highly desirable.

SUMMARY

In certain example aspects described herein, a post-surgical garment comprises a wrap-around design that comprises pouches for comfortable placement of surgical drains. In an example embodiment, the garment specifically meets the needs of patients who have gone through breast or chest surgeries, require post-surgical drains, and/or need to keep the surgical area protected from moisture during showers or sponge baths. The garment provides one solid wrap around piece designed to keep the post-surgical drains and the tubing of the drains secure while showering or during daily activities. In an example embodiment, the garment allows for security of the post-surgical drains and tubing both while showering and during active daily activities. In another example embodiment, the garment securely holds the post-surgical drain tubing and/or bulbs to protect against movement and possible dislodging of the drains. In another example embodiment, the garment also protects the surgical area and drain sutures against direct water contact. In an example embodiment, the garment comprises a top and bottom closure that prevents the water from entering the garment while showering. In another example embodiment, the garment is a tight fitting solid wrap around piece designed to prevent water from entering the garment.

In an example embodiment, the garment may be used at the hospital and at home, enabling a patient to shower and sponge bath with secure placements of post-surgical drains, freedom of movement for both arms, while maintaining a light compression for the breasts or surgical area, and protection from direct water contact to prevent bacteria and infection in the surgical area or the area surrounding the drain sutures.

In an example embodiment, the garment is worn around the torso, shoulders, and/or waist of the patient. In another example embodiment, the garment is worn around features of the body such as the patient's arms, legs, thighs, calves, knees, or other joints in the body.

In an example embodiment, the garment is used by placing one or more straps over a user's shoulders and wrapping the garment around the chest area. A post-surgical drain is slipped through an opening on the side of the garment and any attached tubing is fed through. The post-surgical drain and excess tubing is placed in a pouch. A flap over each opening is securely closed to cover the opening. The garment is then closed in the front with a secure closure. The shoulder straps may be removed from the garment or may be slipped loosely over the shoulders, if desired.

In an example embodiment, the garment comprises a bathing garment that protects the surgical area from water during a shower or sponge bath while still maintaining compression and providing pouches for the surgical drains. In another example embodiment, the garment comprises a bathing garment that both protects the surgical area and provides a placement for surgical drains during a shower. In an example embodiment, the garment is a bathing garment made of neoprene or other water resistant material that is worn while showering or sponge bathing to protect a surgical wound and secure post-surgical drains and tubing. In an example embodiment, top and bottom closures prevent water from entering the garment.

In another example embodiment, the garment is a lounging garment made of a poly-Lycra fabric blend, spandex, cotton, nylon, or other breathable/moisture wicking material that is worn for daily use to protect a surgical wound and secure post-surgical drains and tubing. In an example embodiment, the garment does not provide compression of a wound area.

In an example embodiment, the garment is double lined, with the lining and the outer material sewn together with elastic, cord, or other material sewn to the top and bottom of the garment. In an example embodiment, the elastic band seals the top and/or bottom of the garment to prevent water from entering the inside of the garment.

The garment can comprise one or more straps. In an example embodiment, the straps aid the user in putting the garment on, and may function like bra straps. In an example embodiment, the straps are removable and do not function to hold the garment up after placement on the user. In this embodiment, the straps comprise one or more rings, clips, or adhesive that attach the strap to the garment.

The garment is closed in the front using a secure closure sewn into the garment. In an example embodiment, a VELCRO® hook and loop closure, zipper, or other secure closure is used. In another example embodiment, the closure is water resistant and prevents water from entering the garment through the front closure.

Pouches are sewn onto the front, sides, and/or rear of the garment. In an example embodiment, one pouch is sewn onto the right front of the garment and one pouch is sewn into the left front of the garment. In another example embodiment, one pouch is also sewn onto the back of the garment. In an example embodiment, the pouches are made of a mesh material that allows water to pass through without collecting inside the pouches. In another example embodiment, the pouches are made of a neoprene or other water resistant material. In yet another example embodiment, the pouches are made of a poly-Lycra fabric blend, spandex, cotton, nylon, or other breathable material. In an example embodiment, the pouches are large enough to securely hold one or more post-surgical drains, catheters, colostomy bags, or other medical bags, collection containers, or tubing. In an example embodiment, the pouches cover and conceal the post-surgical drains.

In an example embodiment, each pouch has an elastic band, cord, or other material sewn to the top of the pouch. In an example embodiment, the elastic band secures the contents of the pouch.

An opening or small slit is made on the left and/or right side of the garment for the drains to be pushed through and the tubing to be extended. In an example embodiment, the opening is under the arm of the user or above the pouch. In an example embodiment, the opening or slit proceeds through both layers of the garment and exposes the user's skin.

A flap is sewn onto the garment at the top of each opening. In another example embodiment, the flap is sewn onto the side or bottom of the opening. In an example embodiment, the flap is securely sewn on one side, allowing the user to open and close the flap as needed. In an example embodiment, the flap is made of a neoprene or other water resistant material to prevent water from entering the opening. In another example embodiment, the flap is made of a poly-Lycra fabric blend, spandex, cotton, nylon, or other breathable material.

The flap is secured on the remaining three sides using a secure closure sewn into the garment and into the flap. In another example embodiment, the flap is sewn onto the garment on two or more sides and the flap is secured on the remaining sides using the secure closure. In an example embodiment, a VELCRO® hook and loop closure, zipper, or other secure closure is used. In another example embodiment, the closure is water resistant and prevents water from entering the garment through the flap when it is closed.

These and other aspects, objects, features, and advantages of the example embodiments will become apparent to those having ordinary skill in the art upon consideration of the following detailed description of illustrated example embodiments.

DETAILED DESCRIPTION OF THE EXAMPLE EMBODIMENTS

Example Architectures

The functionality of the various example embodiments will be explained in more detail in the following description, read in conjunction with the figures illustrating the invention. Turning now to the drawings, in which like numerals indicate like (but not necessarily identical) elements throughout the figures, example embodiments are described in detail.

Figure 1:
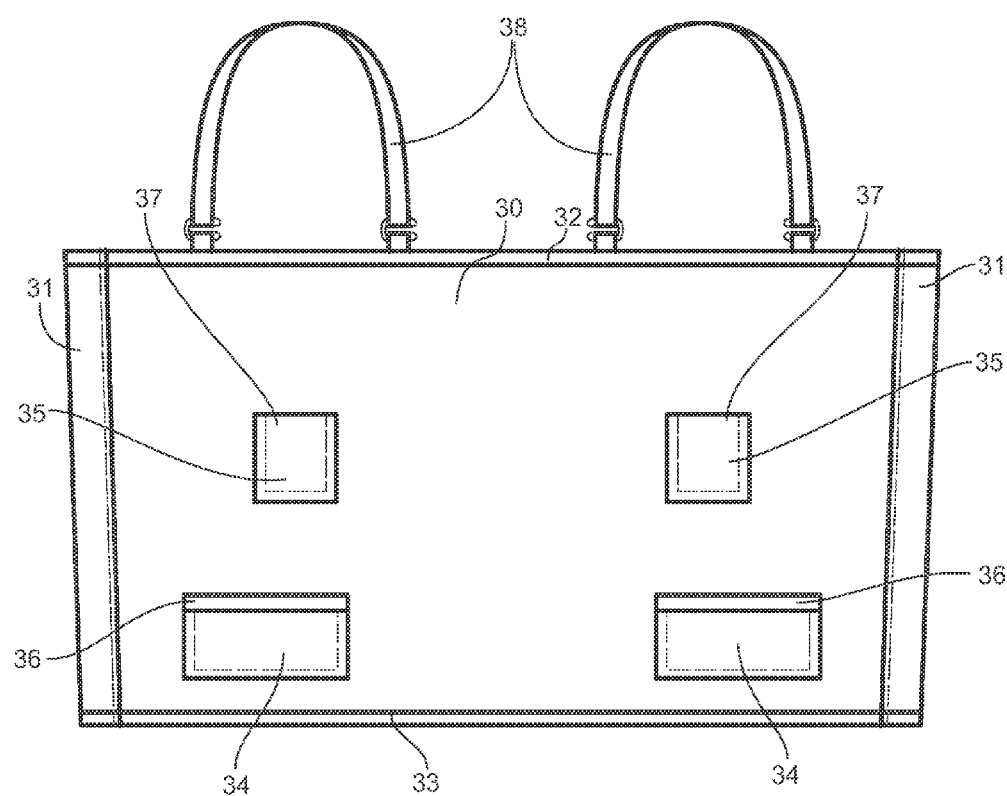
FIG. 1 is an example plan view of a post-surgical garment, in accordance with certain example embodiments.

FIG. 1 is an example plan view of a post-surgical garment, in accordance with certain example embodiments. As depicted in FIG. 1, the example post-surgical garment comprises: a wrap around water resistant material with lining 30, sewn in front closure 31, an elastic trim to seal the top of the garment 32, an elastic trim to seal the bottom of the garment 33, one or more mesh pouches/pockets 34, one or more flaps sewn onto the sides of the garment 35, elastic bands for mesh pockets 36, closures for the sewn in flaps on the sides of the garments 37, and removable straps 38.

Figure 2:
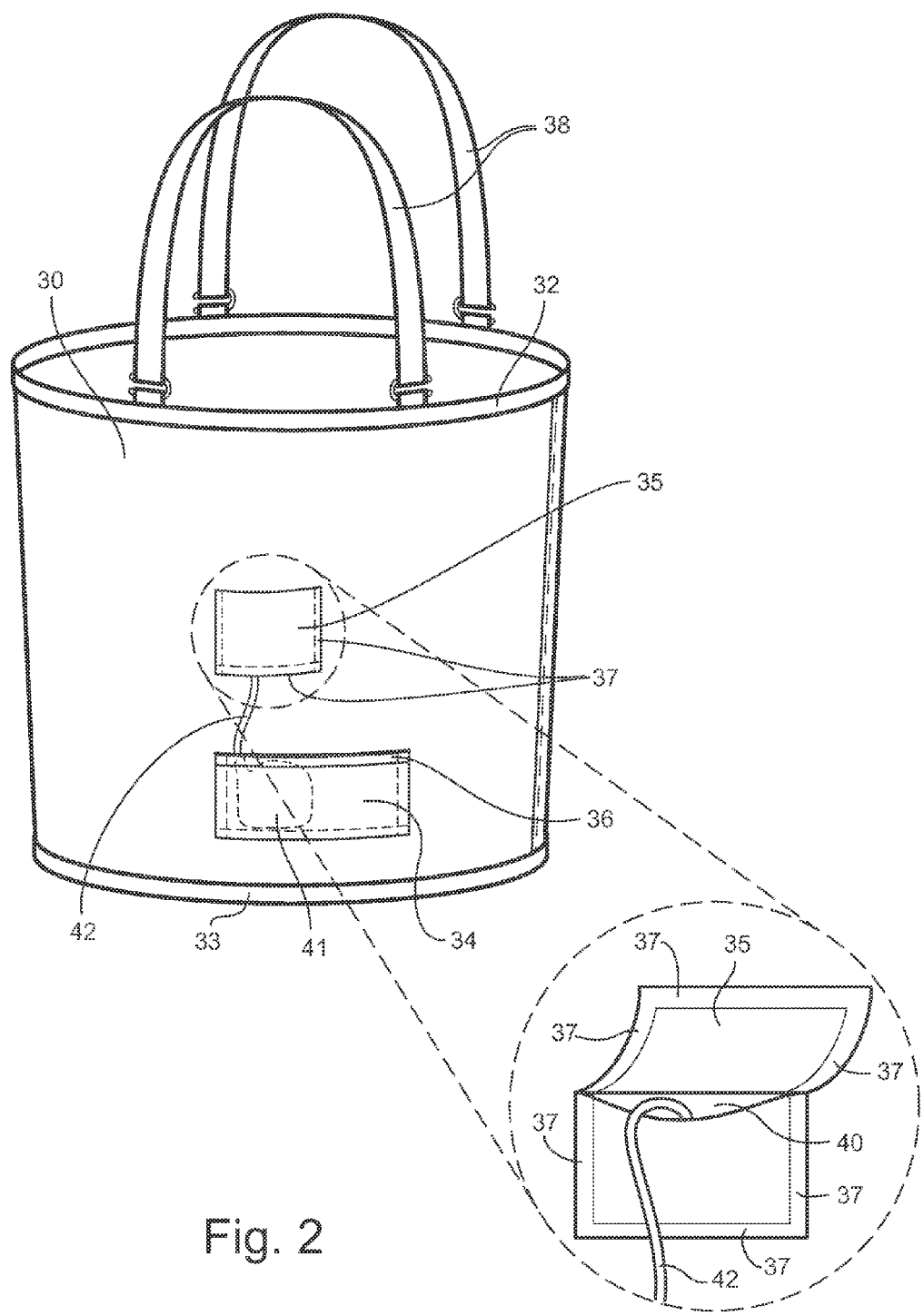
FIG. 2 is an example side plain view of a post-surgical garment with a close view of an opening/flap assembly, in accordance with certain example embodiments.

FIG. 2 is an example side plain view of a post-surgical garment with a close view of an opening/flap assembly, in accordance with certain example embodiments. As depicted in FIG. 2, the example post-surgical garment further comprises: one or more openings or slits on the sides of the garment 40 that are covered by the flaps 35. The one or more post-surgical drains 41 and one or more sets of post-surgical drain tubing 42 are inserted through the openings on the sides of the garment 40 and secured in the one or more mesh pockets 34.

Figure 3:
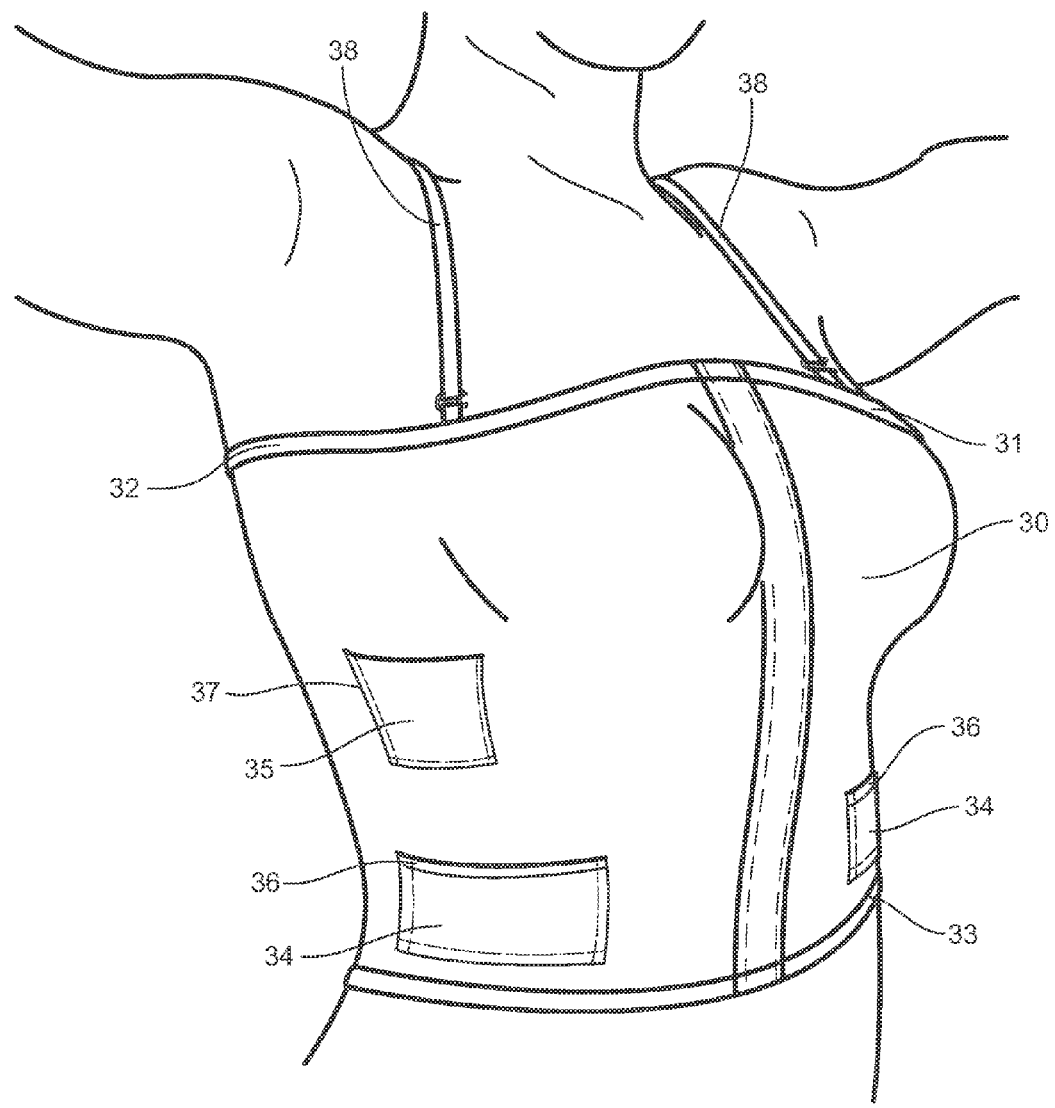
FIG. 3 is an example front/side perspective view of a post-surgical garment, in accordance with certain example embodiments.

FIG. 3 is an example front/side perspective view of a post-surgical garment, in accordance with certain example embodiments. The example front/side perspective view of a post-surgical garment are described with reference to the components illustrated in FIGS. 1 and 2.

The components of the post-surgical garment are described hereinafter with reference to the example embodiments.

Example Embodiments

In an example embodiment, a solid wrap around component 30 is made of water-resistant material and lined with soft material. In another example embodiment, the solid wrap around component 30 is made of a breathable and/or moisture wicking material. The solid wrap around component 30 is connected in the front with an adjustment mechanism 31, for example, sewn in VELCRO® hook and loop closure, zipper, or other secure closure.

In an example embodiment, the wrap 30 is lined at the top and bottom with liners 32, 33. The liners 32, 33 can be sewn in elastic strips, cord, or other material that can match curvature of the body. In an example embodiment, the liners 32, 33 seal the top and bottom of the garment and repel water.

In an example embodiment, pouches 34 are provided, in proximity of the bottom liner 33. The number of pouches 34 can vary. In an example embodiment, the pouches 34 are provided on each side of the wrap 30. For example, two pouches 34 line the bottom of the garment 30 in which to place the post-surgical drains 41. In an example embodiment, the pouches 34 are made of a mesh material that allows water to pass through without collecting inside the pouches. In another example embodiment, the pouches 34 are made of a neoprene or other water resistant material. In yet another example embodiment, the pouches 34 are made of a poly-Lycra fabric blend, spandex, cotton, nylon, or other breathable material. In an example embodiment, the pouches 34 are large enough to securely hold one or more post-surgical drains 41, catheters, colostomy bags, or other medical bags, collection containers, or tubing 42. In an example embodiment, the pouches 34 cover and conceal the post-surgical drains 41. Each pouch 34 can be lined at the top with closure assemblies 36, for example an elastic band, cord, or other material sewn to the top of the pouch 34 or to the garment above the pouch. In an example embodiment, the closure assembly 36 secure the contents of the pouch 34.

In an example embodiment, the side of the garment can have an opening 40, for example, on the right and left side of the garment. In an example embodiment, each opening 40 is large enough to allow the post-surgical drain 41 to be inserted therethrough, for example approximately two inches in length. Each opening 40 can be covered, for example, via sewn on flaps 35. In an example embodiment, the flaps 35 are made of water-resistant material, and lined with a soft material. In another example embodiment, the flaps 35 are made of a breathable or moisture wicking material.

In an example embodiment, each flap 35 is sewn onto the garment at the top of each opening 40. In another example embodiment, the flap 35 is sewn onto the side or bottom of the opening 40. In an example embodiment, the flap 35 is securely sewn on one side, allowing the user to open and close the flap as needed. In an example embodiment, the flap 35 is secured on the remaining three sides using a secure closure 37 sewn into the garment and into the flap 35. In another example embodiment, the flap 35 is sewn onto the garment on two or more sides and the flap 35 is secured on the remaining sides using the secure closure 37. In an example embodiment, a VELCRO® hook and loop closure, zipper, or other secure closure is used. In another example embodiment, the closure 37 is water resistant and prevents water from entering the garment through the flap 35 when it is closed.

In an example embodiment, a user inserts his/her arms through the removable straps 38. The user pushes post-surgical drains 41 through the side slits 40 and places the post-surgical drains 41 in the pouches 34. In an example embodiment, one post-surgical drain 41 is used per pocket. In another example embodiment, two or more drains 41 are used per pocket. The user then wraps the garment 30 around the user's torso and secures the garment 30 with the closure 31 in the front. The user then secures the tubing 42 for the post-surgical drains 41 by closing the flaps 35 on each side of the garment using the secure closure 37.

General

To facilitate an understanding of the principles and features of the various embodiments of the invention, various illustrative embodiments are explained above. Although exemplary embodiments of the invention are explained in detail, it is to be understood that other embodiments are contemplated. Accordingly, it is not intended that the invention is limited in its scope to the details of construction and arrangement of components set forth in the following description or illustrated in the drawings. The invention is capable of other embodiments and of being practiced or carried out in various ways, such as clothing lines, non-bathing garments, and any other embodiments. Also, in describing the exemplary embodiments, specific terminology will be resorted to for the sake of clarity. The garment may be used by adults and children.

It must also be noted that, as used in the specification and the appended claims, the singular forms "a," "an" and "the" include plural references unless the context clearly dictates otherwise. For example, reference to a component is intended also to include composition of a plurality of components. References to a composition containing "a" constituent is intended to include other constituents in addition to the one named.

Also, in describing the exemplary embodiments, terminology will be resorted to for the sake of clarity. It is intended that each term contemplates its broadest meaning as understood by those skilled in the art and includes all technical equivalents which operate in a similar manner to accomplish a similar purpose.

It is also to be understood that the mention of one or more method steps does not preclude the presence of additional method steps or intervening method steps between those steps expressly identified.

The materials described as making up the various elements of the invention are intended to be illustrative and not restrictive. Many suitable materials that would perform the same or a similar function as the materials described herein are intended to be encompassed within the scope of the invention. Such other materials not described herein can include, but are not limited to, for example, materials that are developed after the time of the development of the invention.

The example systems, methods, and acts described in the embodiments presented previously are illustrative, and, in alternative embodiments, certain acts can be performed in a different order, in parallel with one another, omitted entirely, and/or combined between different example embodiments, and/or certain additional acts can be performed, without departing from the scope and spirit of various embodiments as defined in the claims, the scope of which is to be accorded the broadest interpretation so as to encompass such alternatives.

Although specific embodiments have been described above in detail, the description is merely for purposes of illustration. It should be appreciated, therefore, that many aspects described above are not intended as required or essential elements unless explicitly stated otherwise. Modifications of, and equivalent components or acts corresponding to, the disclosed aspects of the example embodiments, in addition to those described above, can be made by a person of ordinary skill in the art, having the benefit of the present disclosure, without departing from the spirit and scope of embodiments defined in the following claims, the scope of which is to be accorded the broadest interpretation so as to encompass such modifications and equivalent structures.

What is claimed is:

1. A post-surgical garment, comprising:
    a body section of material configured to wrap around a user and comprising a closure mechanism that secures the garment around the user, wherein the body section of material is a water-resistant material designed to repel water;
    one or more openings through the material that through which post-surgical materials can be passed from an internal side of the garment to an external side of the garment;
    one or more flaps that are each closable over a corresponding one of the one or more openings; and
    one or more pouches on the external side of the garment in which the post-surgical materials are placed, wherein each of the one or more the pouches comprise a mesh material that allows water to pass through without collecting inside the pouches.

2. The post-surgical garment of claim 1, wherein the post-surgical garment is used while showering or sponge bathing.

3. The post-surgical garment of claim 1, wherein the body section of material is a moisture wicking material.

4. The post-surgical garment of claim 1, wherein each of the one or more flaps is attached to the body section of material at a top of a corresponding one of the one or more openings and secured by a flap closure to the body section of material on a bottom and on each side of the corresponding one of the one or more openings.

5. The post-surgical garment of claim 4, wherein the each of the one or more flaps prevents water from entering to the inside of the garment through each of the one or more openings.

6. The post-surgical garment of claim 1, wherein the closure mechanism is water resistant and prevents water from entering to the inside of the garment.

7. The post-surgical garment of claim 1, wherein the post-surgical materials comprise one or more of a post-surgical drain, a catheter, a colostomy bag, a collection bag, a collection containers, and a tubing.

8. The post-surgical garment of claim 1, wherein at least one of the one or more pouches can hold more than one post-surgical material.

9. The post-surgical garment of claim 1, wherein the material is configured to wrap around a user's torso.

10. The post-surgical garment of claim 1, further comprising:
    a top sealing mechanism disposed on a top of the body section of material that seals a top of the post-surgical garment, wherein the top sealing mechanism prevents water from entering to the inside of the garment through the top of the post-surgical garment; and
    a bottom sealing mechanism disposed on a bottom of the body section of material that seals a bottom of the post-surgical garment around the user, wherein the bottom sealing mechanism prevents water from entering to the inside of the garment through the bottom of the post-surgical garment.

11. The post-surgical garment of claim 10, wherein the top sealing mechanism comprises an elastic material sewn into the top edge of the material.

12. The post-surgical garment of claim 1, further comprising one or more straps disposed on a top of the body section of material.

13. A method of securing post-surgical drains, comprising:
    inserting a post-surgical drain through an opening in a body section of material of a post-surgical garment that wraps around a user, wherein the body section of material is a water-resistant material designed to repel water;
    feeding a post-surgical drain tubing attached to the post-surgical drain through the opening in the body section of material;
    inserting the post-surgical drain into a pouch attached to the body section of material, wherein the pouch comprises a mesh material that allows water to pass therethrough;
    securing a flap over the opening in the body section of material to cover the opening;
    wrapping the body section of material around the user; and
    securing the body section of material around the user with a closure mechanism attached to the material of the post-surgical garment.

14. The method of claim 13, further comprising inserting arms of the user through straps attached to a top portion of the body section of material.

15. The method of claim 13, wherein the body section of material is a moisture wicking material.

16. The method of claim 13, wherein the flap is sewn into the body section of material at a top of the opening and secured to the body section of material on a bottom and on each side of the opening by a flap closure mechanism.

17. The method of claim 13, wherein the flap prevents water from entering through the opening.

18. The method of claim 13, wherein the closure mechanism is water resistant and prevents water from entering the body section of material.

* * * * *